United States Patent
Pawar et al.

(10) Patent No.: US 11,842,427 B2
(45) Date of Patent: Dec. 12, 2023

(54) METHOD AND SYSTEM OF MOTION CORRECTION FOR MAGNETIC RESONANCE IMAGING

(71) Applicant: MONASH UNIVERSITY, Clayton (AU)

(72) Inventors: Kamlesh Pawar, Clayton (AU); Zhaolin Chen, Clayton (AU); Nadim Joni Shah, Clayton (AU); Gary Francis Egan, Clayton (AU)

(73) Assignee: Monash University

( * ) Notice: Subject to any disclaimer, the term of this patent is extended or adjusted under 35 U.S.C. 154(b) by 306 days.

(21) Appl. No.: 17/055,504

(22) PCT Filed: May 14, 2019

(86) PCT No.: PCT/AU2019/050447
§ 371 (c)(1),
(2) Date: Nov. 13, 2020

(87) PCT Pub. No.: WO2019/218000
PCT Pub. Date: Nov. 21, 2019

(65) Prior Publication Data
US 2021/0225047 A1    Jul. 22, 2021

(30) Foreign Application Priority Data
May 15, 2018    (AU) ................. 2018901688

(51) Int. Cl.
*G06T 11/00*    (2006.01)
*G06T 7/246*    (2017.01)
(Continued)

(52) U.S. Cl.
CPC ............ *G06T 11/008* (2013.01); *A61B 5/055* (2013.01); *A61B 5/7207* (2013.01);
(Continued)

(58) Field of Classification Search
CPC ..... G06T 11/008; G06T 7/0012; G06T 7/246; G06T 2207/20081; G06T 2207/20084;
(Continued)

(56) References Cited

U.S. PATENT DOCUMENTS 9,679,373 B2    6/2017    Vilsmeier et al.
2010/0142789 A1*  6/2010    Chang ................ G01R 33/5608
                                                              600/410
(Continued)

FOREIGN PATENT DOCUMENTS

WO    2014195454 A1    12/2014

OTHER PUBLICATIONS

Aizenberg et al., "Type of Blur and Blur Parameters Identification Using Neural Network and its Application to Image Restoration," Institute for Information Transmission Problems of the Russian Academy of Sciences, Aug. 1, 2002, 6 pages.
(Continued)

*Primary Examiner* — Van D Huynh
(74) *Attorney, Agent, or Firm* — Davis Wright Tremaine LLP

(57) ABSTRACT

A method and system for reducing or removing motion artefacts in magnetic resonance (MR) images, the method including the steps of: receiving a motion corrupted MR image; determining a corrected intensity value for each pixel in the motion corrupted MR image by using a neural network; and generating a motion corrected MR image based on the determined corrected intensity values for the pixels in the motion corrupted MR image.

15 Claims, 6 Drawing Sheets

(51) Int. Cl.
*A61B 5/055* (2006.01)
*A61B 5/00* (2006.01)
*G01R 33/48* (2006.01)
*G01R 33/565* (2006.01)
*G06T 7/00* (2017.01)

(52) U.S. Cl.
CPC ........ *A61B 5/7267* (2013.01); *G01R 33/4818* (2013.01); *G01R 33/56509* (2013.01); *G06T 7/0012* (2013.01); *G06T 7/246* (2017.01); *G06T 2207/20081* (2013.01); *G06T 2207/20084* (2013.01); *G06T 2207/20201* (2013.01); *G06T 2207/30004* (2013.01); *G06T 2207/30168* (2013.01)

(58) Field of Classification Search
CPC . G06T 2207/20201; G06T 2207/30004; G06T 2207/30168; G06T 2207/10081; G06T 2207/10088; G06T 2207/10104; G06T 2207/20076; G06T 5/003; A61B 5/055; A61B 5/7207; A61B 5/7267; A61B 5/0033; A61B 5/0042; A61B 5/7271; A61B 6/037; A61B 6/501; A61B 6/5211; A61B 6/5264; G01R 33/4818; G01R 33/56509; G01R 33/5608; G06N 3/0481; G06N 3/0454; G06N 3/08
USPC .......................................... 382/131
See application file for complete search history.

(56) References Cited

U.S. PATENT DOCUMENTS

| | | | |
|---|---|---|---|
| 2017/0099200 A1* | 4/2017 | Ellenbogen | G06V 10/764 |
| 2019/0128989 A1* | 5/2019 | Braun | G06N 3/047 |
| 2019/0287674 A1* | 9/2019 | Nitta | G16H 30/40 |
| 2021/0027436 A1* | 1/2021 | Banerjee | A61B 5/7267 |
| 2021/0177296 A1* | 6/2021 | Saalbach | A61B 5/7207 |
| 2021/0181287 A1* | 6/2021 | Sommer | G06T 5/003 |

OTHER PUBLICATIONS

Andre et al., "Toward Quantifying the Prevalence, Severity, and Cost Associated With Patient Motion During Clinical MR Examinations," Journal of the American College of Radiology, May 2015, 7 pages.

Ehman et al., "Adaptive Technique for High-Definition MR Imaging of Moving Structures," Magnetic Resonance Imaging, Oct. 1989, 9 pages.

Gallichan et al., "Retrospective Correction of Involuntary Microscopic Head Movement Using Highly Accelerated Fat Image Navigators (3D FatNavs) at 7T," Magnetic Resonance in Medicine, Mar. 1, 2016, 10 pages.

Jang et al., "ANFIS : Adap tive-Ne twork-Based Fuzzy Inference System," IEEE Transactions on Systems, Man, and Cybernetics, 23(3): May/Jun. 1993, 21 pages.

Jia et al., "Caffe: Convolutional Architecture for Fast Feature Embedding," Jun. 20, 2014, 4 pages.

Qin et al., "Prospective Head-Movement Correction for High-Resolution MRI Using an In-Bore Optical Tracking System," Magnetic Resonance in Medicine, Oct. 1, 2009, 11 pages.

* cited by examiner

METHOD AND SYSTEM OF MOTION CORRECTION FOR MAGNETIC RESONANCE IMAGING

FIELD

The present invention generally relates to a method and system of motion artefact correction for medical imaging, and in particular magnetic resonance imaging (MRI).

BACKGROUND

Magnetic resonance imaging (MRI) is a medical imaging technique that uses strong magnets and radiofrequency pulses to generate signals from the patient's body and to form pictures of the anatomy and the physiological processes of the body. One of the major challenges in MRI is patient motion during magnetic resonance (MR) data acquisition. The presence of motion during an MRI scan may cause image blurring and incoherent artefacts, and therefore degrade the quality of the obtained image. As a result, repeated scans are often required to achieve diagnostic quality images.

In order to address this problem, various motion correction techniques have been proposed. One known approach includes the use of external devices such as cameras or magnetic probes placed near the MRI scanner to detect and correct for the patient motion during the scan (also known as "intra-frame motion"). However, these external devices usually are expensive, require calibration, and may be difficult to setup, which makes them unsuitable for the use in clinical practice or research imaging centres.

Other existing techniques include k-space based motion correction and image based motion correction, which use k-space navigators and image navigators respectively. These motion correction techniques involve a redesign of the pulse sequence to acquire patient motion information that can be used to subsequently correct for image distortion due to patient motion. Nevertheless, k-space or image navigators may interfere with the MR sequence echo time (TE), repetition time (TR), and other imaging parameters. This may result in low signal to noise (SNR) and increased scan time. Moreover, each MR sequence needs to be redesigned to integrate a k-space or image navigator and, crucially, navigators are not compatible with all the imaging sequences.

It is desired to address or ameliorate one or more disadvantages or limitations associated with the prior art, or to at least provide a useful alternative.

SUMMARY

According to one aspect, the present invention provides a method for reducing or removing motion artefacts in magnetic resonance (MR) images, the method including the steps of:
receiving a motion corrupted MR image;
determining a corrected intensity value for each pixel in the motion corrupted MR image by using a neural network; and
generating a motion corrected MR image based on the determined corrected intensity values for the pixels in the motion corrupted MR image.

According to a second aspect, the present invention provides a system for reducing or removing motion artefacts in magnetic resonance (MR) images, the system including at least one processer configured to:
receive a motion corrupted MR image;
determine a corrected intensity value for each pixel in the motion corrupted MR image by using a neural network; and
generate a motion corrected MR image based on the determined corrected intensity values for the pixels in the motion corrupted MR image.

According to a third aspect, the present invention provides a method for reducing or removing motion artefacts in medical images, the method including the steps of:
receiving a motion corrupted medical image;
determining a corrected intensity value for each pixel in the motion corrupted medical image by using a neural network; and
generating a motion corrected medical image based on the determined corrected intensity values for the pixels in the motion corrupted medical image.

According to a fourth aspect, the present invention provides a system for reducing or removing motion artefacts in medical images, the system including at least one processer configured to:
receive a motion corrupted medical image;
determine a corrected intensity value for each pixel in the motion corrupted medical image by using a neural network; and
generate a motion corrected medical image based on the determined corrected intensity values for the pixels in the motion corrupted medical image.

BRIEF DESCRIPTION OF THE DRAWINGS

Embodiments of the present invention are hereinafter described, by way of example only, with reference to the accompanying drawings, wherein.

DESCRIPTION

An embodiment provides a method and a system for correcting motion artefacts in medical images, such as those produced by an MM machine, by using a deep learning model.

The method and system use a neural network to generate motion corrected MR images based on MR images with motion artefacts (the latter may also be referred to hereinafter as "motion corrupted images").

The neural network is trained to determine a corrected intensity value for each pixel in the motion corrupted MR image, e.g., by using a classification model or a regression model.

For example, when using a classification model, the neural network (which may also be referred to as a "classification network") classifies the intensity of each pixel in the motion corrupted image to a quantized value, the quantized value being one of a plurality of predetermined quantized values of intensity. In this way, the task of motion correction is recast into a pixel classification task. This conversion facilitates the accurate motion correction. The quantized value may have a smaller bit depth compared to the intensity of each pixel in the motion corrupted image. This reduces the memory resources required and the computational complexity. For example, the intensity of each pixel in a motion corrupted image may be represented by a floating point number (e.g., a single-precision floating point number that typically occupies 32 bits, or a double-precision floating point number that typically occupies 64 bits), while the quantized value may be a 8-bit number and accordingly the intensity of each pixel is classified into one of 256 different classes. Alternatively, the reconstructed image may be represented using more bits for each pixel at the expense of memory and computational complexity.

Alternatively, the neural network may use a regression model to determine a corrected intensity value for each pixel in the motion corrupted MR image, in which case the neural network may also be referred to herein as a "regression network". The regression network predicts the corrected intensity value for each pixel based on the intensity value of that pixel in the motion corrupted MR image.

Using the classification model or the regression model, the method and system effectively reduce or remove motion artefacts contained in motion corrupted MR images and generate high-quality motion corrected MR images, without requiring prior estimate of motion parameters or additional sensors.

General Structure

Figure 1:
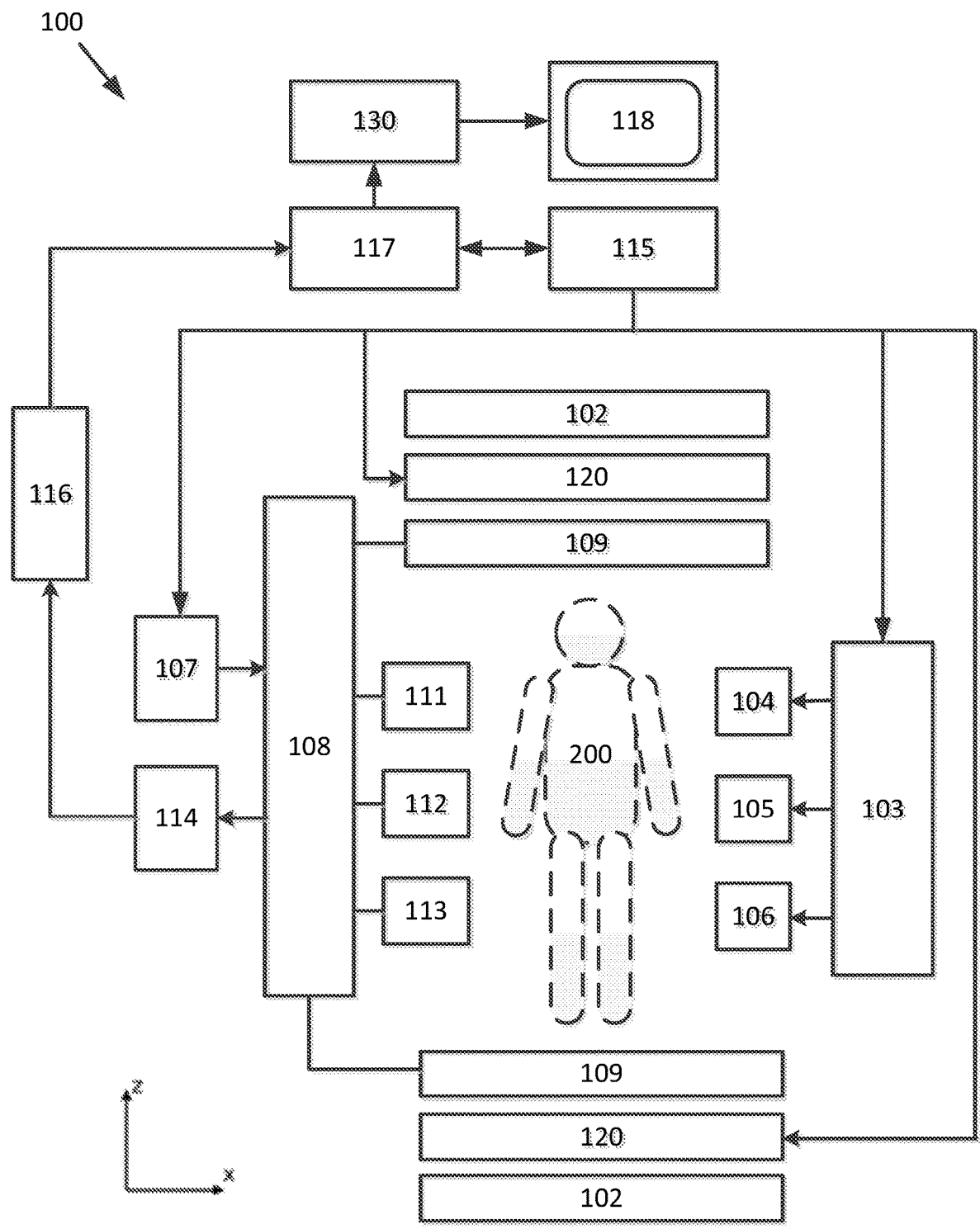
FIG. 1 shows an example of a system for motion correction in MRI.

An example of a system 100 for motion correction in MRI is illustrated in FIG. 1.

In this example, the system 100 also includes components of an MRI machine for carrying out the functions of an MRI scanner, e.g., performing MR scans and acquiring MRI images.

As shown in FIG. 1, the system 100 includes superconducting or resistive main magnet coils 102 for creating a substantially uniform, temporally constant main magnetic field Bo along a z-axis through an examination volume.

The system 100 further includes a set of shimming coils 120. The current flow through the individual shimming coils 120 is controllable to minimize Bo deviations within the examination volume.

A gradient pulse amplifier 103 applies current pulses to selected ones of whole-body gradient coils 104, 105 and 106 along x, y and z-axes of the examination volume. A digital RF frequency transmitter 107 transmits RF pulses or pulse packets, via a send/receive switch 108, to body RF coils 109 to transmit RF pulses into the examination volume. The RF pulses are used to saturate, excite resonance, invert magnetization, refocus resonance, or manipulate resonance and select a portion of a patient's body 200 positioned in the examination volume.

In order to generate MR images of the patient's body 200 by means of parallel imaging, a set of local array RF coils 111, 112, 113 for receiving MR signals are placed contiguous to the region selected for imaging.

The MR signals induced by body-coil RF transmissions are picked up by the array RF coils 111, 112, 113 and/or by the body RF coils 109, and are subsequently demodulated via the send/receive switch 108 by a receiver 114, preferably the receiver 114 including a preamplifier (not shown).

A controller 115, for example in the form of a host computer, controls the shimming coils 120, the gradient pulse amplifier 103 and the transmitter 107 to generate MR imaging sequences, e.g., fast field echo (FFE) sequences.

For the selected sequence, the receiver 114 receives a single or a plurality of MR data lines following each RF excitation pulse.

The received analogue signals of each MR data line are then converted into a digital format by a data acquisition module 116. In some alternative embodiments, the data acquisition module 116 may be formed as a separate device rather than being apart of the system 100.

The digital raw image data is then sent to a processor 117, which reconstructs the digital raw image data in the k-space into an image representation by applying a suitable reconstruction algorithm, for example a Fourier transform, to produce reconstructed MR image data. This reconstructed MR image may represent, for example, a planar slice through the patient, an array of parallel planar slices, a three-dimensional volume, or the like.

The MR image reconstructed by the processor 117 may contain motion artefacts. In order to remove or reduce the motion artefacts, the MR image reconstructed by the reconstruction module 117 is subsequently processed by a motion correction module 130, which generates a motion corrected image based on the motion corrupted input image.

The motion corrected image output by the motion correction module 130 may then be stored in a data store where it can be accessed for converting slices, projections, or other portions of the image representation into appropriate format for visualization, for example via a video monitor 118 which provides a readable display of the resultant MR image.

The motion correction module 130 includes a trained deep learning model for motion correction. Preferably, the motion correction module 130 is embedded in as machine executable instructions and executed by the processor 117 that also performs image reconstruction. The motion correction module 130, in addition to being implemented by embedded firmware, may be implemented by a dedicated hardware, such as an ASIC or FPGA. The processor 117 and module 130 are preferably implemented by a GPU cluster.

Deep Learning Model

Figure 2:
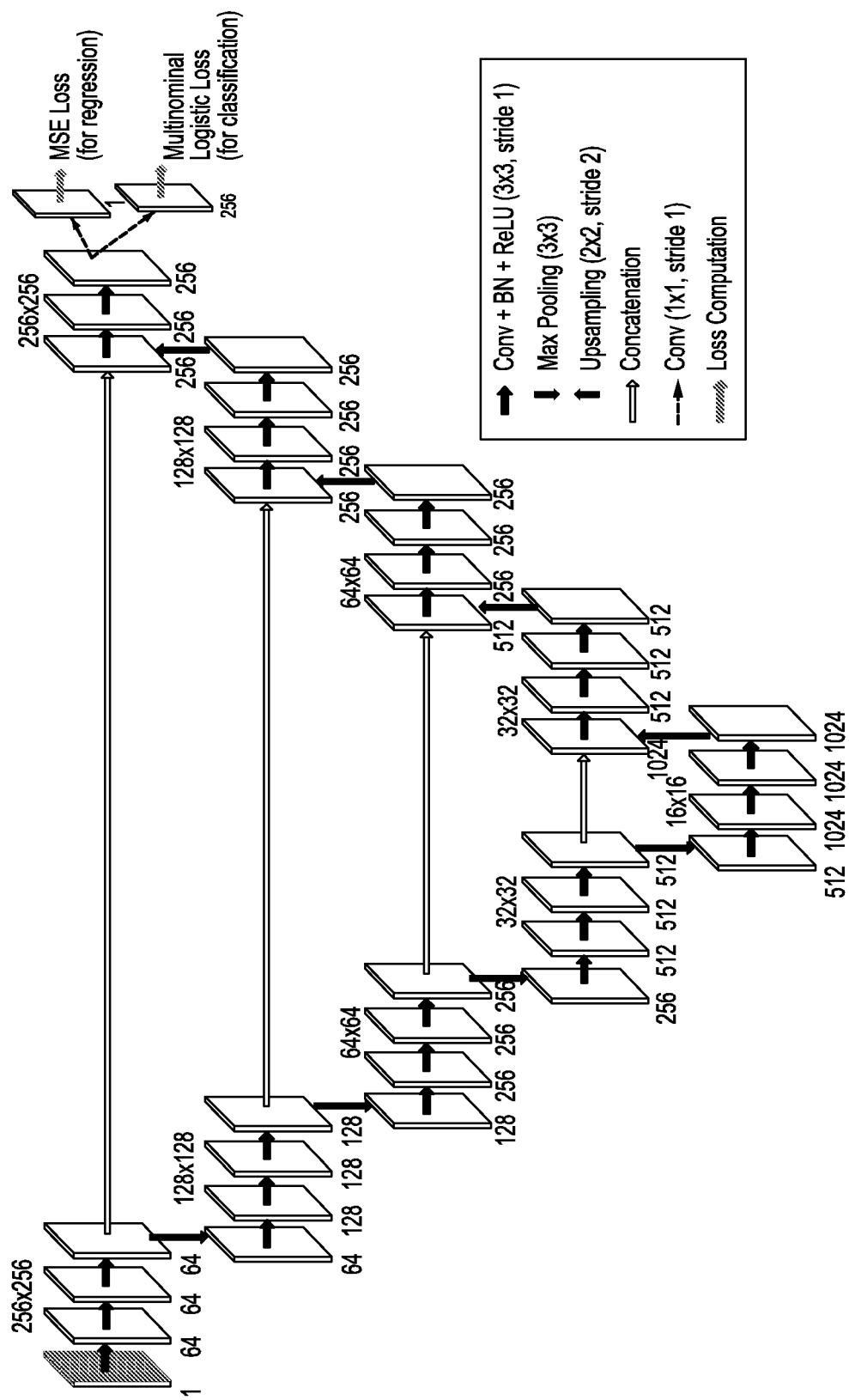
FIG. 2 shows an exemplary architecture of a convolutional neural network for motion correction in MRI.

In this embodiment, the deep learning model of the motion correction module 130 is a convolutional neural network (CNN). FIG. 2 illustrates an exemplary architecture of the CNN.

This CNN architecture is designed and trained for motion correction. The input to the network is 256×256 motion corrupted images with the intensity of each pixel being a floating point number (e.g., a single-precision floating point number that typically occupies 32 bits, or a double-precision floating point number that typically occupies 64 bits).

As described above, the CNN may be a classification network or a regression network. When using a classification network, the output is 8-bit quantized motion corrected images, i.e., the intensity of each pixel in the output image is a 8-bit number. When using a regression network, the intensity of each pixel in the output image is a 32 bit floating point number.

Preferably, the pixel intensity is the grey level intensity of the pixel. However, in some alternative embodiments, the pixel intensity may be the intensity of the pixel in one or more suitable colour channels. In some embodiments, the pixel intensity may include both positive and negative values, e.g., as in phase contrast images.

As shown in FIG. 2, the CNN in this embodiment is an encoder-decoder CNN, having an encoder network (on the left) and a decoder network (on the right) followed by a classification layer or a regression layer.

The encoder network includes a contracting path having a series of convolution and pooling layers. More specifically, the contracting path includes the repeated application of three 3×3 convolutions (stride 2, pad 1). In each level, the 3×3 convolution is followed by a batch normalization (BN) operation and a rectified linear unit (ReLU), and a 3×3 max pooling operation for downsampling. The downsampling halves the height and width dimensions at each successive level. The numbers at the top of each block in FIG. 2 show the resolution of the data and the number at the bottom of each block shows the number of filtered outputs (the filtered outputs may also be referred to as a "feature map").

The decoder network includes an expansive path having a series of 2×2 upsampling operations (stride 2) of the feature map, each followed by a 3×3 convolution with stride 1, a batch normalization operation and a rectified linear unit (ReLU). Each upsampling operation increases the resolution of the corresponding feature map.

In addition to the expansive path, the decoder network also includes a number of concatenation paths which concatenate the upsampled feature maps with the corresponding feature maps passed directly from the encoder network.

In some embodiments, the last layer of the CNN is a classification layer using a 1×1 convolution with stride 1. The classification layer treats the output as a quantized 8-bit image and predicts the probability of each pixel being in one of the 256 different classes. In this way, the classification layer predicts the quantized image intensity level for the motion corrected image. In the training stage, a multinomial logistic loss function is used to evaluate the classification performance of the CNN. Alternatively, any other suitable categorical loss function may be used as the loss function in training the CNN, e.g., Kullback-Leibler (KL) divergence loss.

Alternatively, the last layer of the CNN may be a regression layer that outputs a corrected intensity value for each pixel in the motion corrupted MR image. For a regression network, the loss function used in the training stage may be mean squared error, or any other suitable loss function, such as mean absolute error or mean percentage error.

In total, the encoder-decoder CNN shown in FIG. 2 includes 5 levels (each level shown by a different row of blocks in FIG. 2). Alternatively, in some other embodiments, the encoder-decoder CNN may include any suitable number of levels, depending on the input image size. In the last level, the size of the feature map should be greater than the size of the convolutional kernel. For example, for the 256×256 input image in the above-described example, the CNN may include up to 7 levels to allow the use of a 3×3 convolutional kernel. In the example where the CNN has 7 levels, at level 7, the spatial size of the feature map is 4×4.

Further, in some other embodiments, the encoder-decoder CNN may have any suitable alternative architecture different from the one shown in FIG. 2. For example, variation may be made to one or more characteristics of the CNN architecture, such as the number of CNN layers, the kernel size of convolution, and/or the stride. Additionally, the CNN may have one or more regularization layers, such as dropout layers.

Further, in some other embodiments, the CNN used in the motion correction module 130 may not be an encoder-decoder CNN, but any other suitable type of image to image mapping CNN.

Training of the Deep Learning Model

Figure 3:
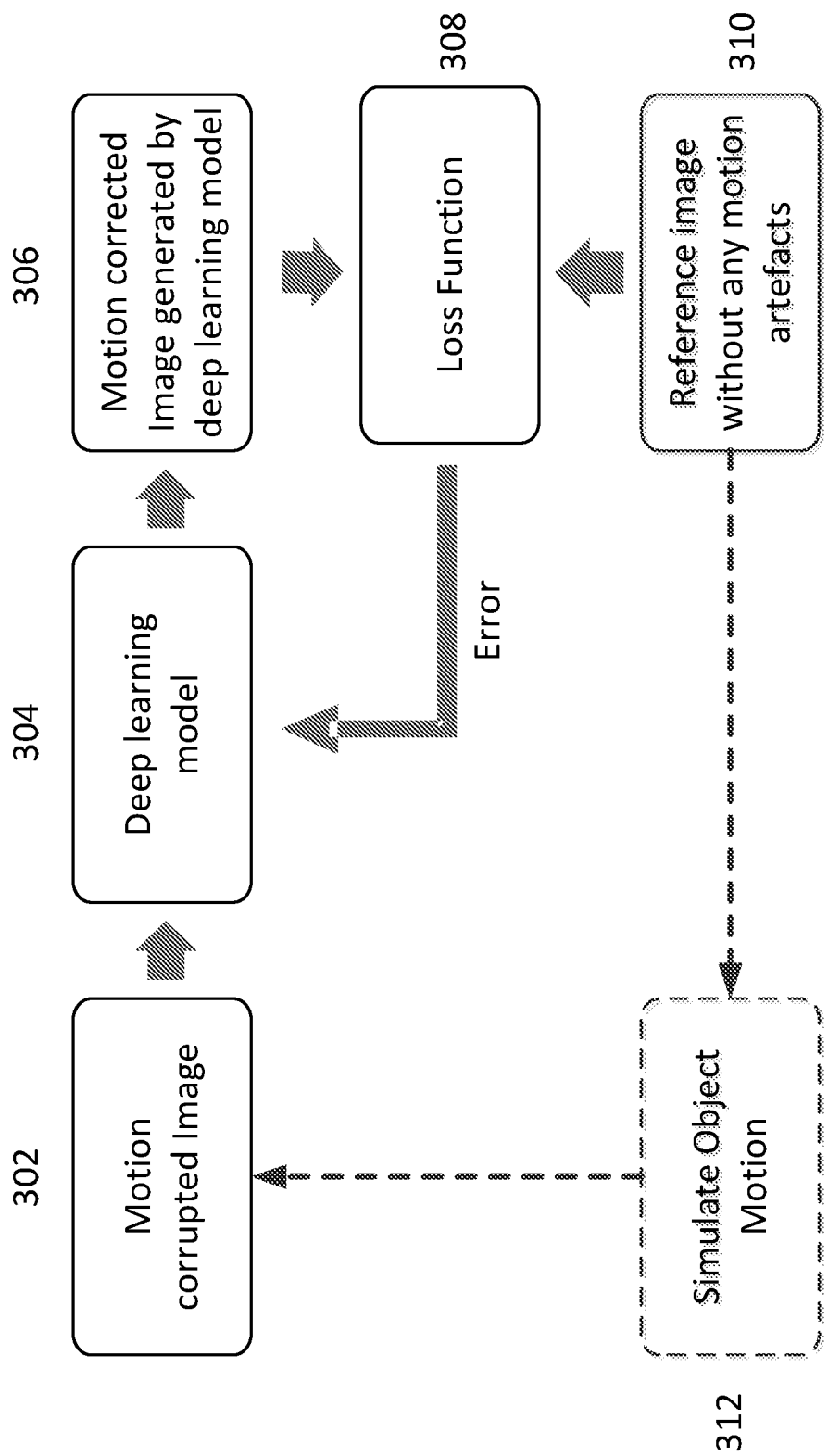
FIG. 3 is a schematic diagram showing the training of a deep learning model for motion correction in MRI.

FIG. 3 is a schematic diagram showing the training of the deep learning model used in the motion correction module 130.

In order to train the deep learning model (304), motion corrupted MR images (302) are produced and fed to the deep learning model (304).

Using the motion corrupted images (302), the deep learning model generates corresponding motion corrected MR images (306). For each motion corrected image, an error is calculated using a loss function (308) based on a corresponding reference MR image that does not contain motion artefacts (310). As described above, for a classification network, the error is calculated using a multinomial logistic loss function or any other suitable categorical loss function; for a regression network, the error may be mean squared error, or error calculated using any other suitable loss function such as KL divergence loss. The error is used to tune the parameters of the deep learning model. The motion correction and tuning process are iterated until desired correction performance is achieved. The tuning of the parameters may be conducted by executing existing CNN training algorithms, such as stochastic gradient descent (SGD), AdaGrad, AdaDelta, RMSProp or other suitable gradient descent optimizers.

As shown by the dashed lines in FIG. 3, each motion corrupted image (302) may be produced by simulating objection motion based on the corresponding reference image without motion artefacts (310).

The training of the deep learning model as shown in FIG. 3 may be performed on external hardware separate from the system 100, for example, a separate graphics processing unit (GPU). After training, the deep learning model is embedded as the motion correction module 130 in the system 100.

Figure 4:
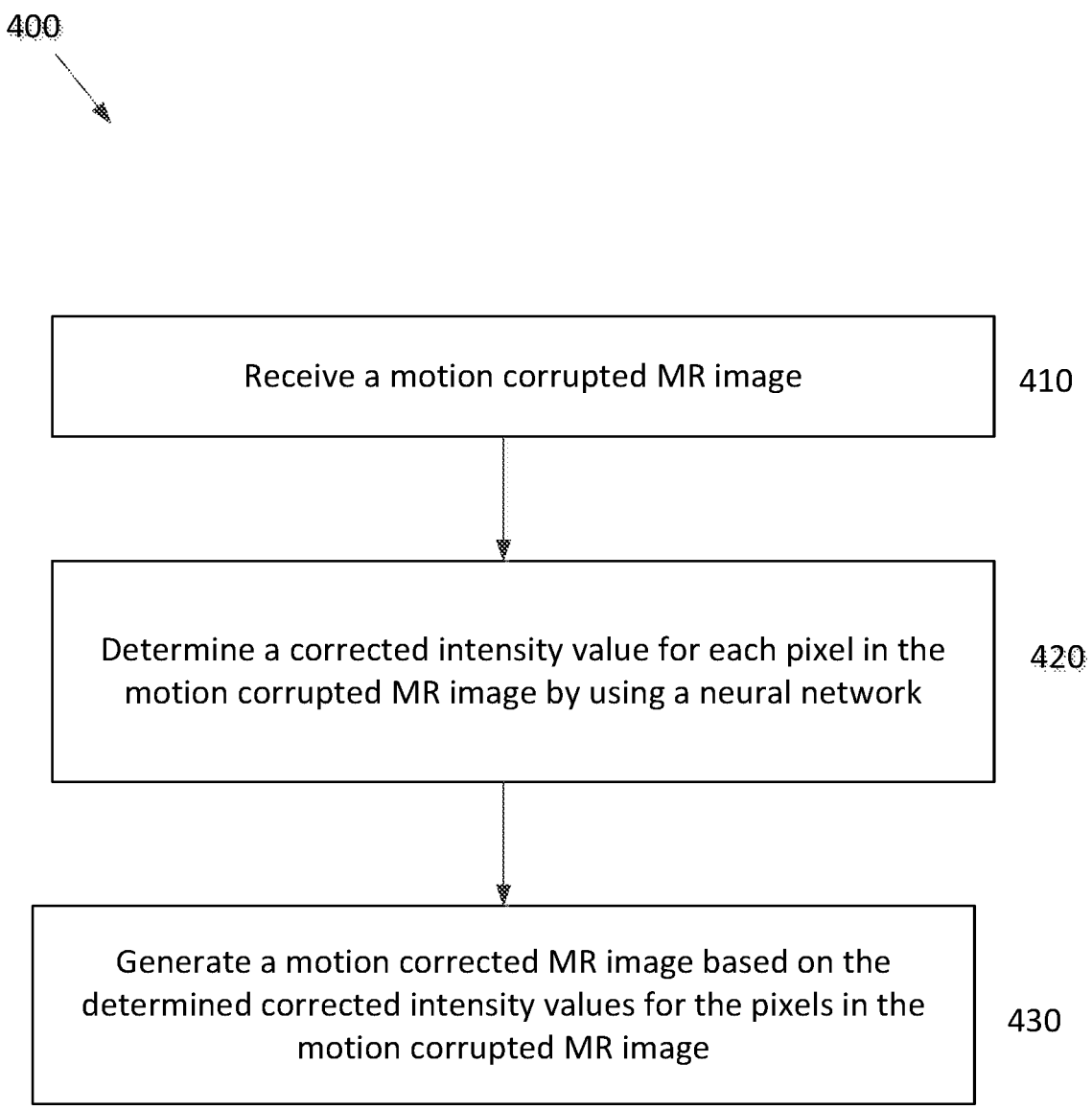
FIG. 4 shows steps executed by a processor in an MR image motion correction process.

FIG. 4 illustrates a motion correction process 400 implemented by the motion correction module 130 of the system 100.

At step 410, the motion correction module 130 receives a motion corrupted MR image.

At step 420, the motion correction module 130 determines a corrected intensity value for each pixel in the motion corrupted MR image by using a neural network.

At step 430, the motion correction module 130 generates a motion corrected MR image based on the determined corrected intensity values for the pixels in the motion corrupted MR image.

Test Examples

Figure 5A:
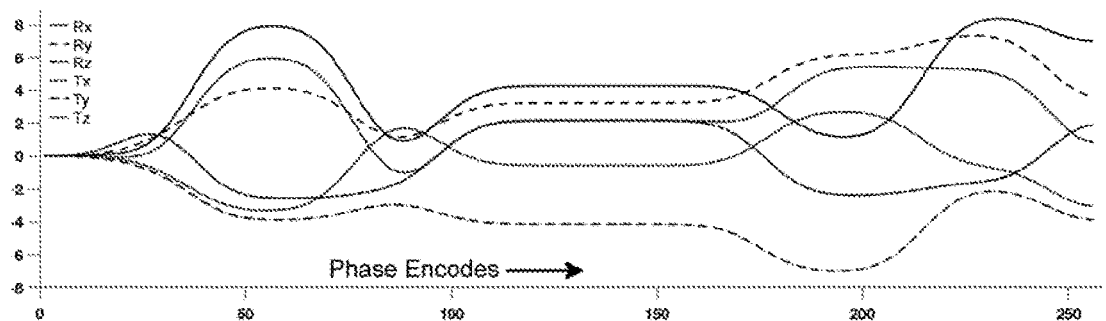
FIGS. 5A and 5B show experimental results of applying motion correction on some MRI test datasets.
Figure 5B:
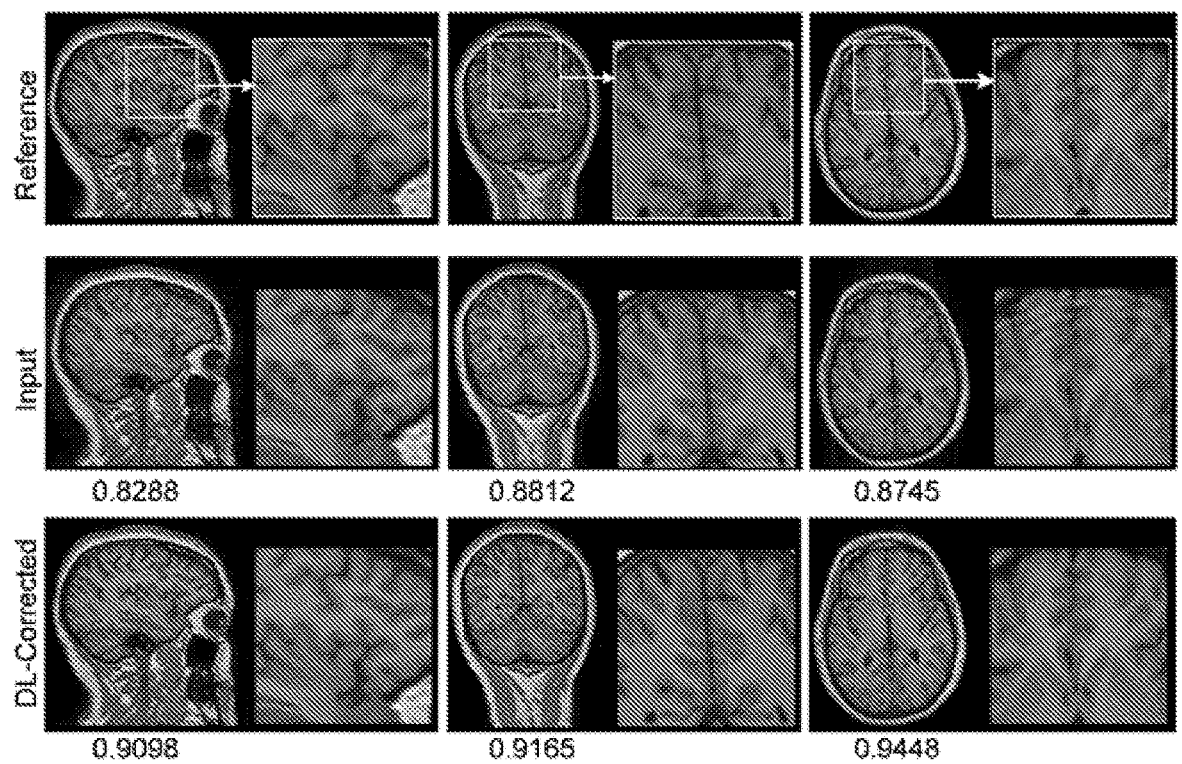

FIG. 5A and FIG. 5B show the experimental results of applying motion correction on test datasets with continuous motion, using the classification network described above.

The plot in FIG. 5A shows the simulated motion parameters, where Rx, Ry, Rz are rotation in degrees, and Tx, Ty, Tz are translation in mm in x, y, z direction, respectively. The x-axis represents time in terms of phase encodes (PE), and the time equal to PE×TR (time of repetition) for MPRAGE sequence.

The three rows in FIG. 5B are, respectively (from top to bottom):

Reference, which shows the motion free clean images;

Input, which shows the images corrupted by the simulated motion; and

DL-corrected, which shows images corrected using the deep learning method as described above.

The numbers in the bottom of images show the corresponding structural similarity (SSIM) scores.

As shown by FIGS. 5A and 5B, the deep learning method described above is able to effectively reduce or remove motion artefacts contained in the motion corrupted images.

Figure 6:
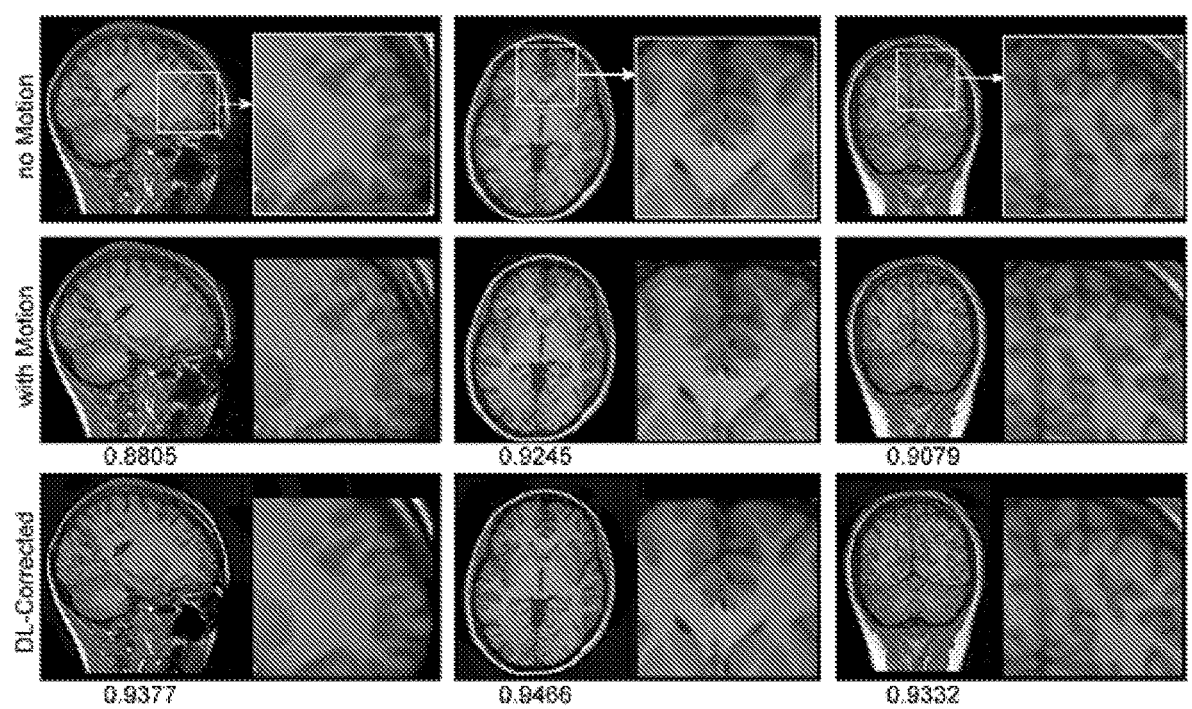
FIG. 6 shows experimental results of applying motion correction on an experimental MRI dataset.

FIG. 6 shows some further results of motion correction applied on an experimental dataset obtained from a volunteer, using the classification network described above. Two scans were performed: one with motion and one without motion.

The three rows in FIG. 5B are, respectively (from top to bottom):
- no motion, which shows images from the scan in which the volunteer did not move;
- with motion, which shows image from the scan in which the volunteer moved randomly at his/her own discretion;
- DL-corrected, which shows images from the scan where the volunteer moved and the motion corrupted images were subsequently corrected using the deep learning network.

The numbers in the bottom of the panels show the SSIM scores with respect to no motion images.

The method and system described herein effectively reduce or remove motion artefacts in MR images without requiring any external sensors or internal navigators.

Compared to existing motion correction techniques such as image or k-space navigators (which may interfere with the MR protocol and penalize contrast, scan time, and SNR), or motion correction methods based on external sensors (which requires calibration and are expensive and complex to setup), the method and system of the embodiments provide a number of advantages.

First, unlike navigators, the method and system do not require development or modification of acquisition sequences or image reconstruction methods. Second, the method and system do not interfere with MR protocol parameters such as T1/T2/TI/TE, scan time or contrast. Third, the method and system do not require any external sensors and thus are relatively inexpensive to be implemented.

The method and system is used to retrospectively, i.e. on reconstruction, correct for motion artefacts in MR images and is complementary to existing MR scanner hardware and software, and may be used as part of the existing pipeline. The described method is able to be used in or with MR scanning machines made by different manufacturers. In use, it significantly improves the efficiency of the machines by correcting for motion as MRI images are generated by the machines.

Further, the deep learning model for motion correction as described herein is not limited to the use in MR images, but may alternatively be used for motion artefact correction for other medical imaging modalities, for example computed tomography (CT) and Positron Emission Tomography (PET).

Further, as described hereinbefore, the deep learning model is not limited to the encoder-decoder CNN or the specific architecture in the described embodiments, but may include any other suitable type of CNN with any suitable architecture.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Many modifications will be apparent to those skilled in the art without departing from the scope of the present invention as hereinbefore described with reference to the accompanying drawings.

The invention claimed is:

1. A method for reducing or removing motion artefacts in magnetic resonance (MR) images, the method including the steps of:
   receiving a motion corrupted MR image;
   determining a corrected intensity value for each pixel in the motion corrupted MR image by using a neural network; and
   generating a motion corrected MR image based at least in part on the determined corrected intensity values for the pixels in the motion corrupted MR image;
   wherein determining the corrected intensity value for each pixel in the motion corrupted MR image includes:
      classifying intensity of each pixel in the motion corrupted MR image to one of a plurality of predetermined quantized values of intensity by using the neural network, the corrected intensity value of each pixel being the corresponding classified quantized values of intensity.

2. The method of claim 1, wherein the neural network is a convolutional neural network (CNN).

3. The method of claim 2, wherein the CNN is an encoder-decoder CNN that includes an encoder network and a decoder network.

4. The method of claim 3, wherein the encoder network includes a series of convolution and pooling layers, each pooling layer being subsequent to a corresponding convolution layer.

5. The method of claim 3, wherein the decoder network includes a series of upsampling and convolution layers, each convolution layer being subsequent to a corresponding upsampling layer.

6. The method of claim 5, wherein the decoder network concatenates output of each upsampling layer with a corresponding feature map generated by the encoder network.

7. The method of claim 1, wherein the motion corrupted MR image is an image reconstructed based at least in part on motion corrupted k-space data.

8. The method of claim 1, wherein each of the predetermined quantized values of intensity has a smaller bit depth than the intensity of each pixel in the motion corrupted MR image.

9. The method of claim 3, wherein the CNN further includes a pixel intensity classification layer subsequent to the decoder network.

10. The method of claim 1, wherein the neural network is trained by using a multinomial logistic loss function.

11. The method of claim 1, further including:
   receiving raw MR signals generated during a magnetic resonance imaging (MM) scan;
   converting the received raw MR signals into digital MR image data; and wherein
   generating the motion corrupted MR image based at least in part on the determined corrected intensity values for the pixels in the motion corrupted MR image is further based on reconstructing the digital MR image data.

12. A system for reducing or removing motion artefacts in magnetic resonance (MR) images, the system including at least one processor configured to:
   receive a motion corrupted MR image;
   determine a corrected intensity value for each pixel in the motion corrupted MR image by using a neural network; and
   generate a motion corrected MR image based at least in part on the determined corrected intensity values for the pixels in the motion corrupted MR image;

wherein in determining the corrected intensity value for each pixel in the motion corrupted MR image, the at least one processer is further configured to:
classify intensity of each pixel in the motion corrupted MR image to one of a plurality of predetermined quantized values of intensity by using the neural network, the corrected intensity value of each pixel being the corresponding classified quantized values of intensity.

13. The system of claim 12, wherein the system is an MR scanning machine.

14. A method for reducing or removing motion artefacts in medical images, the method including the steps of:
receiving a motion corrupted medical image;
determining a corrected intensity value for each pixel in the motion corrupted medical image by using a neural network; and
generating a motion corrected medical image based at least in part on the determined corrected intensity values for the pixels in the motion corrupted medical image;
wherein determining the corrected intensity value for each pixel in the motion corrupted medical image includes:
classifying intensity of each pixel in the motion corrupted medical image to one of a plurality of predetermined quantized values of intensity by using the neural network, the corrected intensity value of each pixel being the corresponding classified quantized values of intensity.

15. A system for reducing or removing motion artefacts in medical images, the system including at least one processer configured to:
receive a motion corrupted medical image;
determine a corrected intensity value for each pixel in the motion corrupted medical image by using a neural network; and
generate a motion corrected medical image based at least in part on the determined corrected intensity values for the pixels in the motion corrupted medical image;
wherein in determining the corrected intensity value for each pixel in the motion corrupted medical image, the at least one processor is further configured to:
classify intensity of each pixel in the motion corrupted medical image to one of a plurality of predetermined quantized values of intensity by using the neural network, the corrected intensity value of each pixel being the corresponding classified quantized values of intensity.

* * * * *